US00PP12228P2

(12) United States Plant Patent
Utecht

(10) Patent No.: US PP12,228 P2
(45) Date of Patent: Nov. 27, 2001

(54) GERANIUM PLANT NAMED 'FISLULU'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/323,145

(22) Filed: Jun. 1, 1999

(51) Int. Cl.[7] ..... A01H 5/00
(52) U.S. Cl. ..... Plt./332
(58) Field of Search ..... Plt./332, 324

(56) References Cited

FOREIGN PATENT DOCUMENTS

| | | |
|---|---|---|
| 98-1357 | 4/1998 | (CA) . |
| 98-26-1423 | 4/1998 | (CH) . |
| PEL 1349 | 7/1996 | (DE) . |
| 97/0873 | 8/1997 | (EP) . |
| 322 | 4/1998 | (PL) . |

OTHER PUBLICATIONS

Licensing agreement for 'Fislulu', http://www.sicasov.com/baremes/f–fl9899.htm, 1998/1999.*
UPOV–ROM GTIM Computer Database 1999 Database 1999/02, GTI Jouve Retrievel Software, citations for 'Fislulu', 1996–1998.*
Pelargonium 1998, Pelfi Fischer, Hillscheid Germany, p. 16 (1998/1999).

* cited by examiner

*Primary Examiner*—Howard J. Locker
*Assistant Examiner*—Anne Marie Grünberg
(74) *Attorney, Agent, or Firm*—Foley & Lardner

(57) ABSTRACT

A new and distinct cultivar of geranium plant named 'Fislulu', as described and illustrated, and particularly characterized by the combined features of large, deep burgundy, double flowers in uniformly shaped inflorescence, intense green and distinctly zoned foliage, good branching ability, moderate vigorous growth, and medium spring flower response.

1 Drawing Sheet

BACKGROUND OF THE INVENTION

The present invention comprises a new and distinct cultivar of geranium plant, botanically known as *Pelargonium peltatum*, and hereinafter referred to by the cultivar name 'Fislulu'.

'Fislulu' is a product of a planned breeding program which had the objective of creating new geranium cultivars with purple flower color, moderate growth, and relatively early flowering response.

'Fislulu' was originated from a hybridization made by the inventor, Angelika Utecht, in a controlled breeding program in Galdar, Gran Canaria, Spain, in 1993. The female parent was an unnamed hybrid, No. 2275-2, characterized by single, dark-purple flowers, medium-green, zoned foliage, moderately vigorous growth, and medium flowering response. It was derived from crossing the variety 'Fismanon' (U.S. Plant Pat. No. 7,391) with a hybrid seedling derived from crossing a self-seedling of the commercial variety 'Rigi' (unpatented) with the common commercial variety 'Martine' (unpatented). The male parent of 'Fislulu' was the patented cultivar 'Fisan' (U.S. Plant Pat. No. 8,327) having light-violet, double flowers, distinctly zoned foliage, moderate growth, and early flowering response.

'Fislulu' was discovered and selected as one flowering plant within the progeny of the stated cross by the inventor, Angelika Utecht, in spring 1994 in a controlled environment in Galdar, Gran Canaria, Spain.

The first act of asexual reproduction of 'Fislulu' was accomplished when vegetative cuttings were taken from the initial selection in May 1994 in a controlled environment in Galdar, Gran Canaria, Spain by Angelika Utecht. Horticultural examination of plants grown from cuttings of the clone initiated in May 1995 in Hillscheid, Federal Republic of Germany, and continuing thereafter, has demonstrated that the combination of characteristics as herein disclosed for 'Fislulu' are firmly fixed and are retained through successive generations of asexual reproduction.

BRIEF DESCRIPTION OF THE INVENTION

The following traits have been repeatedly observed and are determined to be basic characteristics of 'Fislulu', which in combination distinguish this geranium as a new and distinct cultivar:

1. Deep burgundy flower color;
2. Large semi-spherically shaped inflorescence and large, double florets;
3. Medium green foliage with glossy surface and with distinct zonation;
4. Moderately short and compact, round, well-branched and semi-trailing plant habit;
5. Medium spring flowering response; and
6. Good branching characteristics.

'Fislulu' has not been observed under all possible environmental conditions. The phenotype of the new cultivar may vary significantly with variations in environment such as temperature, light intensity and daylength without any change in the genotype of the plant. The following observations, measurements, and comparisons describe plants grown in Hillscheid, Germany, and in Langley, British Columbia, Canada, under greenhouse conditions which approximate those generally used in commercial practice.

Of the many commercial cultivars known to the present inventor, the most similar in comparison to 'Fislulu' is the patented variety 'Fislu' (U.S. Plant Pat. No. 8,305). In comparison to 'Fislu', 'Fislulu' has:

(a) A relatively close main flower color, with the lower surface somewhat more intensely colored, and with less tendency to fading, thus appearing somewhat more intense;

(b) Relatively large, semi-spherically shaped umbels, in contrast to the smaller, irregularly shaped inflorescence of 'Fislu';

(c) Larger, differently shaped and distinctly zoned leaves;

(d) No tendency to developing edema;

(e) Longer internodes, but shorter branches and shorter plant habit; and (f) Earlier spring flowering response.

BRIEF DESCRIPTION OF THE DRAWING

The accompanying color photographic drawing shows typical flower and foliage characteristics of 'Fislulu' with colors being as true as possible will illustrations of this type.

DETAILED BOTANICAL DESCRIPTION

The measurements were taken in Langley, British Columbia, Canada, on May 26, 1998—10 weeks after planting of rooted cuttings into 15-cm pots. The plants had not been pinched. In the following description, color references are made to The Royal Horticultural Society Colour Chart (R.H.S.). The color values were determined indoors from flowers developed in a greenhouse in May 1998 in Hillscheid, Germany.

Classification:

*Botanical.*—A hybrid of the species *Pelargonium peltatum L'Hérit.*

*Commercial.*—Ivy geranium, cv. 'Fislulu'.

Inflorescence:

*Umbel.*—Shape: (Flat) Semi-spherical. Average diameter: 105 mm. Average depth: 55 mm. Peduncle length: 183 mm. Peduncle color: Medium-green, RHS 143 A–B. Peduncle texture: Relatively thin, smooth surface, with no or very weak pubescence. Pedicel length: 29 mm long with swelling/joint. Pedicel color: Mainly green, RHS 137 B–137 C, reddish line, near RHS 180 B, may run from the 'joint' up to the base of the largest sepal on one side of the pedicel. Number of flowers per umbel: Approximately 7–10. Lastingness of the individual umbel: 7–10 flowers or buds in various stages of development; the individual umbel lasts approximately 15 days in greenhouse conditions in spring at a temperature of 18° C.

*Corolla.*—Average diameter: 52 mm. Form: Double. Shape: Large, round. Number of petals: 12–14. Number of petaloids: 2–3. Color (general tonality from a distance of three meters): Deep burgundy. Color of upper petals: RHS 61 A, slightly iridescent with blackish or bluish tinge in parts, may fade somewhat, though relatively little for a variety of this color group. Markings of upper petals: Weak black stripes (veins) at the base of the upper petals. Color of lower petals: RHS 66 A. Color of lower surface of petals: RHS 66 A–74 B, or lighter. Color of sepals: Light-green, RHS 143 B–C, usually without anthocyanin. Number of sepals: Usually 6. Texture of sepals: Smooth, only weak pubescence.

*Bud (immediately before unfolding of the petals).*—Shape: Narrow, elliptical. Color (sepals): Medium to light green, RHS 137 D–143 A. Color (petals): Dark-red to blackish-purple, approximately RHS 187 C–D. Length: 24 mm. Width: 11 mm.

*Reproductive organs.*—Androecium: 3–7fertile anthers, white to light-pink filaments, yellow-orange pollen. Gynoecium: 5–6-lobed stigma, dark-purple, RHS 59 A, whitish style. Fertility/seed set: Hardly any spontaneous seed set.

*Spring flowering response period.*—In Hillscheid, Germany, in 1998, plants had on average 0.5 flowers opened 15 weeks after planting of unrooted cuttings.

*Outdoor flower production.*—Medium (fair for a variety with large inflorescence).

*Blooming habit.*—Continuous flowering from about May to mid-September; after which flowering may be poor depending on general conditions and light intensity. There is no fragrance noticeable.

*Lastingness of the individual bloom.*—The floret does not drop its petals easily (no shattering); the bloom lasts approximately 8 days in greenhouse conditions in spring at a temperature of 18° C.

*Durability.*—Good shatter resistance, relatively good rain resistance, but only average resistance to burning of flowers by heat (for the red-purple flower color group).

Plant:

*Foliage.*—Form: Ivy-shaped, nearly round, with only very weak lobes and with overlapping base, nearly flat, smooth and glossy surface. Texture: Smooth and glossy surface. Margin: Mainly entire. Size of leaf: 79 mm wide. Color of upper surface: Medium-green, approximately RHS 137 B. Color of lower surface: RHS 137 C–D . Color of zonation: Reddish-brown, approximately RHS 166 A, distinctness is medium. Tolerance of botrytis: Fair.

*General appearance and form.*—Plant habit: Moderately short and compact, round and well-branched; only semi-trailing. Internode length: 30–40 mm. Branching pattern: 7.9 naturally-occuring branches. Length of plants: 55 cm (in late August, based on 32-week-old plants).

I claim:

1. A new and distinct cultivar of geranium plant named 'Fislulu', as described and illustrated.

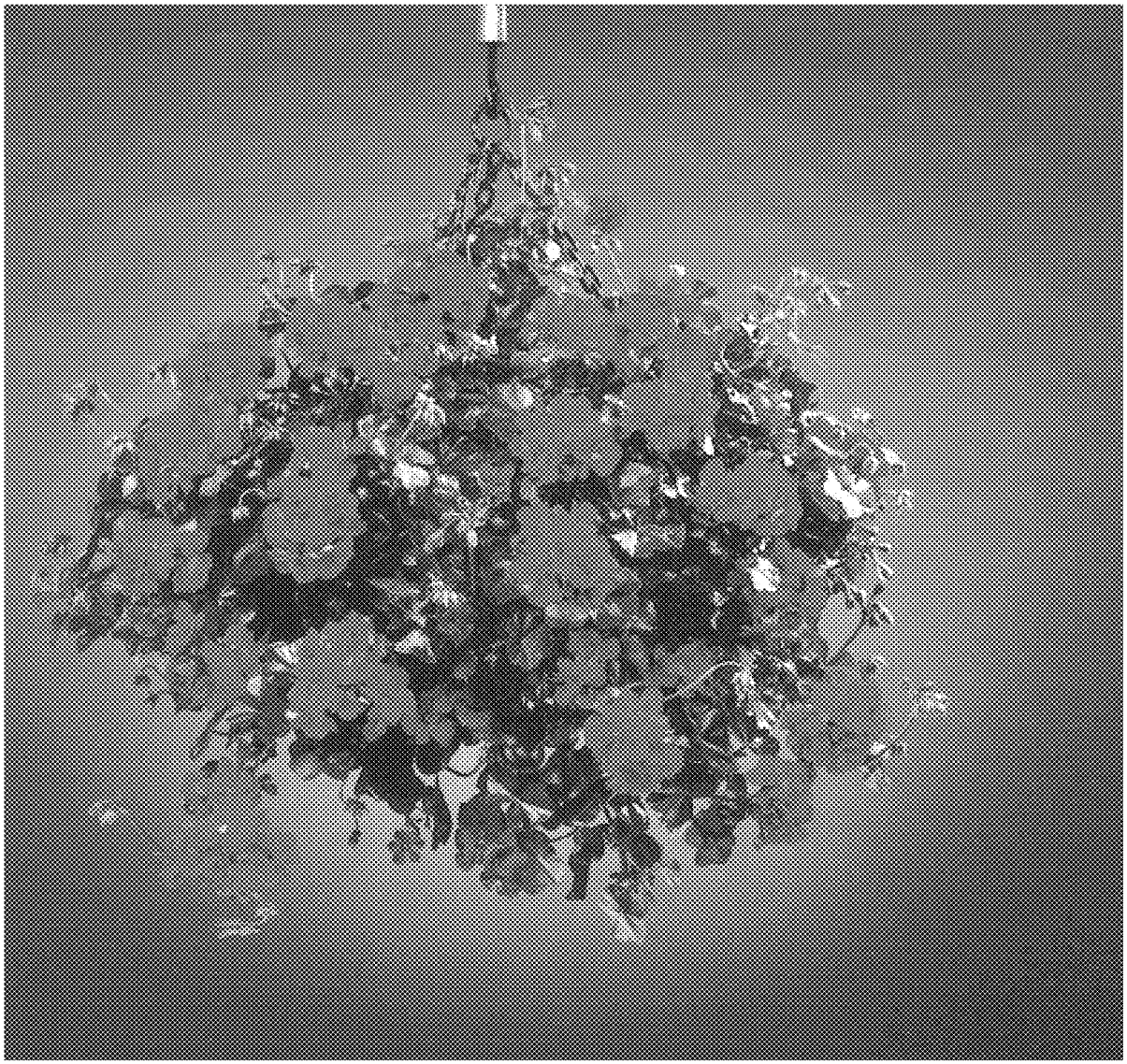

* * * * *